United States Patent
Van Leeuwen et al.

(10) Patent No.: US 12,229,948 B2
(45) Date of Patent: Feb. 18, 2025

(54) SENSITIVITY ANALYSIS FOR DIGITAL PATHOLOGY

(71) Applicant: KONINKLIJKE PHILIPS N.V., Eindhoven (NL)

(72) Inventors: Marinus Bastiaan Van Leeuwen, Eindhoven (NL); Reinhold Wimberger-Friedl, Waalrenl (BE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 740 days.

(21) Appl. No.: 17/057,787

(22) PCT Filed: May 29, 2019

(86) PCT No.: PCT/EP2019/063972
§ 371 (c)(1),
(2) Date: Nov. 23, 2020

(87) PCT Pub. No.: WO2019/229126
PCT Pub. Date: Dec. 5, 2019

(65) Prior Publication Data
US 2021/0366107 A1    Nov. 25, 2021

(30) Foreign Application Priority Data
May 30, 2018    (EP) .................................... 18175126

(51) Int. Cl.
*G06T 7/00* (2017.01)
*G01N 21/31* (2006.01)
(Continued)

(52) U.S. Cl.
CPC ........... *G06T 7/0012* (2013.01); *G01N 21/31* (2013.01); *G01N 21/6486* (2013.01);
(Continued)

(58) Field of Classification Search
CPC ..................... G06T 7/0012; G06T 7/00; G06T 2207/20076; G06T 2207/10064;
(Continued)

(56) References Cited

U.S. PATENT DOCUMENTS

| 5,792,660 A | 8/1998 | Spillert |
| 9,224,098 B2 | 12/2015 | Segall |

(Continued)

FOREIGN PATENT DOCUMENTS

| CN | 101489480 A | 7/2009 |
| CN | 103841411 A | 6/2014 |

(Continued)

OTHER PUBLICATIONS

PCT International Search Report, International application No. PCT/EP2019/063972, Aug. 9, 2019.

(Continued)

*Primary Examiner* — Tuan H Nguyen
(74) *Attorney, Agent, or Firm* — Sherry Austin

(57) ABSTRACT

The ability to obtain and digitise pathology samples (such as in histopathology or cytopathology) has opened up the possibility of accurate and automated computer operated analysis, or computer-assisted analysis, when diagnosing a wide range of medical conditions. A typical digital pathology image analysis pipeline involves a large number of image pre-processing and processing operations. Small changes in the parameters used in these algorithms might lead to significant changes in the eventual pathological finding. Accordingly, the present application proposes to perform a sensitivity analysis on a digital pathology image analysis pipeline to assess the sensitivity of a given pathology result to changes of parameters in the digital pathology image analysis pipeline.

14 Claims, 4 Drawing Sheets

(51) Int. Cl.
G01N 21/64 (2006.01)
G16H 10/40 (2018.01)
G16H 30/00 (2018.01)
*G01N 21/17* (2006.01)

(52) U.S. Cl.
CPC .............. *G16H 10/40* (2018.01); *G16H 30/00* (2018.01); *G01N 2021/1765* (2013.01); *G06T 2207/10064* (2013.01); *G06T 2207/20076* (2013.01)

(58) Field of Classification Search
CPC ........ G16H 10/40; G16H 30/00; G01N 21/31; G01N 21/64; G01N 21/6486; G01N 2021/1765
See application file for complete search history.

(56) References Cited

U.S. PATENT DOCUMENTS

| | | |
|---|---|---|
| 9,754,383 B1 | 9/2017 | Hagendorn |
| 9,792,681 B2 | 10/2017 | Bryan |
| 10,475,183 B2 | 11/2019 | Kawaguchi |
| 11,304,604 B2 | 4/2022 | Dimaio |
| 2005/0130192 A1 | 6/2005 | Paterson |
| 2007/0270707 A1 | 11/2007 | Belalcazar |
| 2011/0010187 A1 | 1/2011 | Andersson |
| 2013/0030305 A1* | 1/2013 | Yu ................. A61B 5/4244 600/476 |
| 2019/0234966 A1* | 8/2019 | Steen ................ G01N 33/6896 |

FOREIGN PATENT DOCUMENTS

| | | |
|---|---|---|
| CN | 105550651 A | 5/2016 |
| EP | 2720192 A1 | 4/2014 |
| WO | WO9729447 A2 | 8/1997 |
| WO | WO2016138041 A2 | 9/2016 |

OTHER PUBLICATIONS

Anonymous: "Otsu's method—Wikipedia", Jan. 12, 2017 (Jan. 12, 2017), XP055468978, Retrieved from the Internet: URL:https://en.wikipedia.org/w/index.php?title=Otsu's_method&oldid=759649503 [retrieved on Apr. 20, 2018].

Anonymous: "Sensitivity Analysis—Wikipedia", Wikipedia, May 23, 2018 (May 23, 2018), XP055526790, Retrieved from the Internet: URL:https://en.wikipedia.org/w/index.php?title=Sensitivity_(control_systems)&oldid=842648445.

Anonymous: "Thresholding (image processing)—Wikipedia", Wikipedia, May 8, 2018 (May 8, 2018), XP055526471, Retrieved from the Internet: URL:https://en.wikipedia.org/w/index.php?title=Thresholding_(image_processing)&oldid=840213467.

Macenko M. et al., "A Method for Normalizing Histology Slides for Quantitative Analysis", Proceedings of ISBI 2009, pp. 1107 to 1110, IEEE 2009, 978-1-4244-3932-4/09.

Dako (TM) (Agilent Technology Solutions (TM)) "Interpretation Manual for PD-L1 IHC 22C3 pharmDx is CE-IVD-Marked".

* cited by examiner

SENSITIVITY ANALYSIS FOR DIGITAL PATHOLOGY

CROSS-REFERENCE TO RELATED APPLICATIONS

This patent application claims the priority benefit under 35 U.S.C. § 371 of International Patent Application no. PCT/EP2019/063972, filed May 29, 2019, which claims the benefit of European Patent Application No. EP18175126.4, filed on May 30, 2018. These applications are hereby incorporated by reference herein in their entirety.

FIELD OF THE INVENTION

The present invention relates to an apparatus for processing digital pathology image data to generate pathology score data and the sensitivity analysis of the pathology score data, and an associated method, a digital pathology system, a computer program element, and a computer readable medium.

BACKGROUND OF THE INVENTION

In the field of pathology, a continuing trend is the automation of aspects of the analysis of digital pathology images. Digital image processing techniques are well-suited to analysing large numbers of input images in a standardised manner. However, such approaches are highly dependent on variations in the initial preparation of the sample used to obtain the pathology image (such as the exact techniques and conditions present when preparing, storing, and examining a histopathlogy slide, for example).

Here reference is made to sensitivity analysis, where further background details can be found for example in the article on sensitivity analysis https://en.wikipedia.org/wiki/Sensitivity_analysis. Sensitivity analysis is the study of how the uncertainty in the output of a mathematical model or system (numerical or otherwise) can be divided and allocated to different sources of uncertainty in its inputs.

In computer vision Otsu's method, see for example, https://en.wikipedia.org/wiki/Otsu%27s_method, named after Nobuyuki Otsu 大津展之 Ōtsu Nobuyuki), is used to automatically perform clustering-based image thresholding, or, the reduction of a graylevel image to a binary image. The algorithm assumes that the image contains two classes of pixels following bi-modal histogram (foreground pixels and background pixels), it then calculates the optimum threshold separating the two classes so that their combined spread (intra-class variance) is minimal, or equivalently (because the sum of pairwise squared distances is constant), so that their inter-class variance is maximal. Consequently, Otsu's method is roughly a one-dimensional, discrete analog of Fisher's Discriminant Analysis. Otsu's method is also directly related to the Jenks optimization method.

US2013/0030305A1 describes a method for determining a stage of fibrosis in a liver. The method comprises the steps of: obtaining input data relating to the liver, the input data being generated using a second harmonic generation based imaging system; identifying a plurality of morphological features of the liver from the input data relating to the liver; generating a plurality of measurements based on the identified plurality of morphological features; and determining the stage of fibrosis in the liver based, on the generated plurality of measurements.

WO2016/138041A2 describes methods, systems, and devices for evaluating the status of cells in a sample involving imaging of cells, transformation of cell images into biophysical metrics, and transformation of the biophysical metrics into prognostic indications on the cellular and subject levels. Automated apparatus, processes, and analyses are also described.

The publication "A Method for Normalizing Histology Slides for Quantitative Analysis" by Macenko, et al., published in the proceedings of ISBI 2009, pp. 1107 to 1110, IEEE 2009, 978-1-4244-3932-4/09 discusses digital processing techniques aimed at overcoming known inconsistencies in histopathlogy staining process. However, such techniques may be further improved.

SUMMARY OF THE INVENTION

There is, therefore, need to improve digital pathology imaging approaches.

The object of the present invention is solved by the subject-matter of the appended independent claims, wherein further embodiments are incorporated in the dependent claims.

According to a first aspect, there is provided an apparatus for digitally processing digital pathology image data to generate pathology score data, and a sensitivity analysis of the pathology score data. The apparatus comprises:

an input unit; and
a processing unit.

The input unit is configured to obtain digital pathology image data comprising an image of a pathology sample.

The processing unit is configured to classify objects in the digital pathology image data into a plurality of candidate objects, to assign a first pathological state to at least one candidate object in the plurality of candidate objects according to one or more detection thresholds and/or detection probabilities, to obtain initial pathology score data of the pathology sample based on the candidate objects in the plurality of candidate objects having been assigned the first pathological state, to perturb the one or more detection thresholds and/or the detection probabilities according to a perturbation function to generate a perturbed detection threshold and/or a perturbed detection probability, to reassign the first pathological state to at least one candidate object in the plurality of candidate objects according to the one or more perturbed detection thresholds and/or perturbed detection probabilities, to obtain updated pathology score data of the pathology sample based on the candidate objects having been reassigned the first pathological state according to the one or more perturbed detection thresholds and/or the perturbed detection probabilities, and to compare the initial pathology score data and the updated pathology score data to obtain a sensitivity of the pathology score data.

Accordingly, it is possible to generate and to provide feedback about the sensitivity of pathology score data to realistic variations in one or more thresholds used in an analysis that has been used to produce the score. The thresholds may, for example, be related to the probability of pixel or area classification of an object in a digital pathology image. Optionally or in combination, the thresholds may be related to the intensities and/or wavelengths that represent the expression of a biomarker in a pathological sample.

In other words, as well as automatically generating a pathology score enabling a diagnosis of a condition to be performed on the basis of a digital pathology image, a medical professional may be provided with an assessment of how sensitive the pathology score is to minor changes in the analysis. This may be particularly important when an output pathology score is at or near a boundary value, where a pathology score slightly above or slightly below the boundary value could lead to alternative treatment options. A medical professional may use the information about the sensitivity of the pathological technique in decision-making and reporting, and optionally may perform a manual inspection of indicated problematic areas. Therefore, the pathology process is made faster and more reliable.

Optionally, the one or more detection thresholds and/or detection probabilities characterise a variation in automatic morphological feature detection when determining the presence of a candidate object in the digital pathology image data.

Accordingly, the sensitivity of a pathological scoring approach when detecting features such as cells, cell nuclei, or membranes can be tested. A morphological feature detection algorithm such as "morphological closing" may have several input arguments altering its effectiveness. By generating several versions of the morphological feature detection using an initial input argument, and randomly perturbed input arguments, the sensitivity of the pathological scoring approach to the morphological feature detection algorithm when considered with a specific digital pathology image may be considered.

Optionally, wherein the one or more detection thresholds characterise a probability of automatic classification of the objects in the digital pathology image data into the plurality of candidate objects.

Optionally, the detection threshold and/or the detection probability characterise an intensity level and/or a wavelength range of light emitted from a pathology sample and represented in the digital pathology image data.

Typically, a pathology sample is treated with a biomarker that stains a sample a first colour when the biomarker is in contact with a material target, and that stains a sample a second colour (or does not stain) when the biomarker is not in contact with material target. Such staining may be observed for example using a light microscope and/or a fluorescence microscope (in the case of a fluorescently tagged biomarker). Changes in the biomarker application protocol, sample preparation, storage and/or viewing all lead to sensitivity in the provision of a pathological score. Accordingly, in this optional embodiment it is possible to assess the effect of changes in an intensity level and/or a wavelength range of light emitted from a pathology sample on the final pathological score relating to that sample.

Optionally, the intensity level and/or the wavelength range emitted from the pathology sample and represented in the digital pathology image data indicate a relative level of the expression of a biomarker.

Optionally, the processing unit is further configured to obtain a plurality of perturbed detection thresholds and/or perturbed detection probabilities forming a sensitivity function of the pathology score of the digital pathology image data and optionally, and to compute a relative detection threshold change necessary to provide a change in the pathology score.

Accordingly, generating a sensitivity function based on a plurality of perturbed detection thresholds enables a rate of change of a sensitivity function to be assessed as a rate of change of one, or more of the detection thresholds and/or probabilities, rather than at discrete thresholded points. From this, optimum thresholds for specific sample types and other analysis settings can be provided which are the least likely to lead to unpredictable changes in the pathology score, for example Optionally, the processing unit is further configured to obtain the initial pathology score data and/or the updated pathology score data by counting the number of candidate objects in a field of interest of the digital pathology data having been assigned the first pathological state before and/or after perturbation, or by calculating a percentage score of the number of candidate objects in a field of interest of the digital pathology data having been assigned the first pathological state before and/or after perturbation.

Optionally, the processing unit is further configured to assign a second pathological state to at least one candidate object showing positive expression of a first biomarker of interest, to assign a third pathological state to at least one candidate object showing negative expression of the first biomarker of interest, to obtain the initial pathology score data by performing a calculation using the candidate objects in the field of interest of the digital pathology data in the second and third pathological states, to perturb the detection thresholds used to assign the second and third pathological states to the candidate objects and to reassign the second and third pathological states to the candidate objects after perturbation, and to obtain updated pathology score data by performing a calculation using the candidate objects in the second and third pathological states after perturbation.

Histopathology protocols involving the measurement of negative and positive biomarker expression are complicated to perform, and thus the effect of variable measurement thresholds in the sample preparation and digital image processing of the digital pathology images may lead to more accurate assessment of the results of such complicated protocols.

Optionally, the apparatus further comprises:
an output unit.

The output unit is configured to output the sensitivity of the pathology score data to a user, optionally in combination with the initial and/or updated pathology score data and/or outputting the sensitivity of the pathology score relative to a clinical threshold.

Accordingly, the medical professional is quickly and conveniently provided with an assessment of the sensitivity of a pathological test to internal test variations. Hitherto, the effect of threshold variations on pathological tests have been difficult to perceive.

Optionally, the processing unit is further configured to spatially sub-sample the digital pathology image data into a plurality of sectors, and to obtain initial pathology score data and updated pathology score for each sector, to generate a spatial sensitivity mask of the digital pathology image data using the initial pathology score data and updated pathology score for the each sector. The output unit is configured to display the spatial sensitivity mask to a user, optionally as a semi-transparent overlay in spatial alignment superimposed over the digital pathology image data.

Accordingly, an intuitive and user-friendly assessment of the effect of the sensitivity of a pathology analysis pipeline to threshold variation is provided to a medical professional when generating pathology score data from a digital pathology image may be provided.

Optionally, the pathology sample is a histopathology sample or a cyto(path)ology sample.

According to a second aspect, there is provided a digital pathology system.

The digital pathology system comprises:
a digital pathology image acquisition device; and
an apparatus according to the first aspect or one of its embodiments.
wherein the digital pathology scanner is configured to receive a pathology sample, to automatically analyze the pathology sample and to thus acquire digital pathology image data, and to communicate the digital pathology image data to the apparatus.

According to a third aspect, there is provided a method for digitally processing digital pathology image data to generate pathology score data, and a sensitivity analysis of the pathology score data. The method comprises:

a) obtaining digital pathology image data comprising an image of a pathology sample;
b) classifying objects in the digital pathology image data into a plurality of candidate objects;
c) assigning a first pathological state to at least one candidate object in the plurality of candidate objects according to one or more detection thresholds and/or detection probabilities;
d) obtaining initial pathology score data of the pathology sample based on the candidate objects in the plurality of candidate objects having been assigned the first pathological state;
e) perturbing the one or more detection thresholds and/or the detection probabilities according to a perturbation function to generate a perturbed detection threshold and/or a perturbed detection probability;
f) reassigning the first pathological state to at least one candidate object in the plurality of candidate objects, or to at least one candidate object in a perturbed plurality of candidate objects, according to the one or more perturbed detection thresholds and/or perturbed detection probabilities; and
g) obtaining updated pathology score data of the pathology sample based on the candidate objects having been assigned the first pathological state according to the one or more perturbed detection thresholds and/or the perturbed detection probabilities, and comparing the initial pathology score data with the updated pathology score data to obtain a sensitivity of the pathology score data.

Optionally, the method is method for processing digital histopathology image data to generate histopathology score data, and a sensitivity analysis of the histopathology score data.

Optionally, the method is method for processing digital cytopathology image data to generate cytopathology score data, and a sensitivity analysis of the cytopathology score data.

According to a fourth aspect, there is provided a computer program element comprising instructions which, when the program is executed by a computer or a processing unit, cause the computer to carry out the method of the third aspect.

According to a fifth aspect, there is provided a computer readable medium having stored thereon the computer program element of the fourth aspect.

In the following application, the term "digital pathology image data" means a digital representation of a pathology slide obtained using a digital light microscope or a digital fluorescent microscope, for example. Many scanners can support resolutions of between 10× and 40× magnification. An image file associated with a 20× scan of a 15 mm×20 mm specimen is as large as 3.6 GB. The images may be compressed to more manageable sizes using JPEG-2000 compression, for example. The images are typically accompanied with meta data containing a scan parameters, scan plan, and the like. In digital histpathology images, identifiers defining sections of the part, block and stain type may be comprised in the meta data.

In the following application, the term "pathology" refers to the diagnosis of medical conditions by examining tissue, cell, and body fluid samples. In particular, "histopathology" refers to the preparation of a biopsy tissue specimen in, for example, a resin block which is then cleaved into successive slices prepared on glass slides. "Cytopathology" refers the examination of free cells or tissue micro fragments.

In the following application, the term "pathology score data" means the examination of pathology (histopathological, cytopathological) images to provide a likelihood of a certain medical condition being present. A pathology score may be derived by examining a histopathology slide and counting a number of objects of interest, such as cells or cell nuclei meeting a condition for some disease to present, as opposed to the number of cells that do not meet the condition. As such, a pathology score can be provided as a cell count per unit area of a digital pathology image, or as a percentage, for example.

In the following application, the term "clinical threshold" means that a pathology score indicates that a medical condition is present based upon the counting of objects of interest identified in the digital pathology image data. Typically, the achievement of a clinical threshold may be used to decide upon different forms of medical treatment.

In the following application, the term "sensitivity analysis" means an assessment of how a pathology score changes, and/or the rate at which pathology score changes, when internal thresholds in an algorithm used to determine or to generate the pathology score are changed (or perturbed). Such internal thresholds may not be visible to an end-user of a digital pathology system. In addition, in complicated protocols, there may be so many internal thresholds that the complexity of changes to those thresholds, and their effects on the digital pathology image data processing pipeline quickly overwhelms even an experienced user. A sensitivity analysis therefore provides a realistic assessment of how changes (perturbations) to parameters used in the analysis pipeline can affect the pathology score.

Accordingly, in the following application the term "sensitivity function" means the relationship between the level of internal thresholds in the analysis pipeline, and their effect on the pathology score as applied to the same input digital pathology image data.

In the following application, the term "perturbation" means a change made to one or more of the internal thresholds of the digital pathology image analysis pipeline. Skilled reader will appreciate that the number and type of internal thresholds of a digital pathology image analysis pipeline is highly dependent on the protocol being performed by the analysis pipeline. In a simple case, an image analysis pipeline may receive as an input a digital histopathology image stained with haematoxylin conventionally thresholded at an absorption level of 0.1. A simple example of a perturbation would be to change the threshold used to threshold the digital histopathology image at a level of 0.095, or 0.15. This simple perturbation will cause more or fewer features in the input digital histopathology image to be present, and so any subsequent classification or morphology algorithm will detect a greater or lesser number of cells, for example, leading to a change in the eventual pathology score.

Of course, a complicated analysis pipeline might have 10 or 100 individual thresholds or decision probabilities capable of variation, leading to a highly-dimensional possible perturbation space. One approach to providing the perturbations is the sensitivity analysis approach of varying one decision threshold or decision probabilities out of many over a given uncertainty range, and recording the effect on the pathology score. This process may be repeated for the other thresholds or decision abilities. Although this technique is simple, it does not analyse the full input space because it does not assess the simultaneous variation of thresholds. Of course, other more complicated sensitivity analysis techniques such as regression analysis or partial derivative analysis across the entire perturbation space could also be applied.

In the following application, the term "automatic morphological feature detection" means an algorithm capable of identifying candidate objects in a digital pathology image such as cells, cell nuclei, cell membranes (whether complete or partial), and the like. Techniques such as morphological opening or morphological closing, may be used to perform automatic morphological feature detection. Of course, these algorithms have many input parameters defining their performance, and all or some of these input parameters may be perturbed as part of a sensitivity analysis.

In the following application, the term "biomarker" in the context of this application means an object or molecule detected in a pathology (histopathology, cytopathology) sample enabling the specific detection (isolation) of a particular expressed protein or other biological signal. The object or molecule may, for example, be detected by means of the binding of a fluoro-active protein to a biomarker target, or by the staining of a biomarker target with a stain targeting the biomarker.

In the following application, the term "digital pathology image acquisition device" (or digital pathology image scanner) means a specialised and automated digital optical analysis system capable of providing high-resolution and high-quality digital images of pathology slides, for example, histopathologically prepared slides or alternatively cytopathology samples. A digital pathology image acquisition device may be connected via a computer network to a PACS system, for example to enable further analysis of the images acquired on remote computers in a computer network.

Accordingly, it is a basic idea of the application to provide a feedback mechanism that warns a user (for example, a pathologist) in cases where the automatic assessment of a digital pathology image is a high risk of being inaccurate owing to internal thresholds of the image processing algorithms used. It is proposed to represent the sensitivity of the pathology score with respect to chosen thresholds of algorithms used in analysis pipeline so that a pathologist can take this into consideration when establishing a diagnosis.

These, and other aspects of the present invention will become apparent from, and elucidated with reference to the embodiments described subsequently.

BRIEF DESCRIPTION OF THE DRAWINGS

Exemplary embodiments of the invention will be described with reference to the following drawings.

DETAILED DESCRIPTION OF EMBODIMENTS

Figure 1:
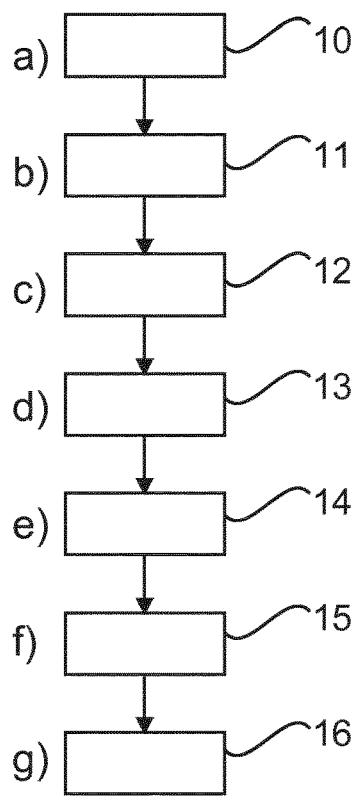
FIG. 1 shows a schematic illustration of a method in accordance with a third aspect.

Immunohistochemical staining is widely used in the diagnosis of abnormal cells such as those found in cancerous tumours. Specific molecular markers are characteristic of particular cellular events such as proliferation or cell death (apoptosis). Visualising an antibody antigen interaction can be accomplished in a number of ways. In the most common instance, an antibody is conjugated to an enzyme, such as peroxidase, that can catalyse a colour-producing reaction (immunoperoxidase staining) alternatively, the antibody can also be tagged to a fluorophore such as fluorescein or rhodamine (immunofluorescence).

The article "PD-L1 Immunohistochemistry Assays for Lung Cancer: Results from Phase 1 of the Blueprint PD-L1 IHC Assay Comparison Project" by Hirsch, et. al, in the Journal of Thoracic Oncology, Vol. 12, No. 2, pp. 208-222 discusses the analytical and clinical comparability of four PD-L1 IHC assays used in clinical trials.

Particular staining protocols are benchmarked to enable a pathological score to be obtained based on a pathology sample. For example, the publication by Dako™ (Agilent Technology Solutions™) "Interpretation Manual for PD-L1 IHC 22C3 pharmDx is CE-IVD-Marked" discusses a quantitative immunohistochemical essay using monoclonal mouse anti-PD-L1 Clone 22C3 for the detection of PD-L1 in formalin-fixed, paraffin-embedded non-small cell lung cancer and melanoma tissue, and the use of this test to derive a "Tumour Proportion Score" as an indicator for treatment with "KEYTRUDA™". However, the skilled person will appreciate that many pathology protocols involving staining are available and will benefit from the application of the technique discussed in this application. The PD-L1 test discussed in this application is provided as an example.

Referring, for example, to FIG. 21 of the "Interpretation Manual for PD-L1 IHC 22C3 pharmDx is CE-IVD-Marked", there is shown an example of PD-L1 stained tissue. The brown colour indicates overexpression of the PD-L1 marker at the cell membrane. The arrows indicate local variation in the strength of expression of the marker. The blue cells are coloured using a counter stain.

In general, the scoring of immunohistochemical markers involves two steps. Firstly, the segmentation of cells or regions of interest is performed (for example, based on their appearance). Secondly, quantification of the stain colour intensity in the region of interest is performed. Typically, a distinction is made between two or more levels of intensity. As an example, in the case of "Her2" staining, four levels (0, 1+, 2+, and 3+) are distinguished based on an amount of the colour intensity at the membrane of tumour cells, and which area fraction of the membrane is stained. Similar principles are applied to nuclear staining protocols like ER and PR.

A typical immunohistochemical assessment has a number of critical steps. For example, viable tumour cells may need to be distinguished from other cell types. Alternatively or in combination, cells expressing a certain biomarker need to be distinguished from cells not expressing a certain biomarker. These assessments may be performed digitally by analysing a digital pathology image using image processing algorithms. However, the image processing algorithms may have one or more decision thresholds.

For example, in may be necessary to decide how to classify nuclei as belonging to a viable tumour cell. The resulting probability may be thresholded at 0.5, but other levels can be selected such as a lower (or more conservative) or a higher (more aggressive) threshold. Optionally, detection thresholds and/or detection probabilities applied in the digital imaging algorithms may be set according to benchmarking using expert judgement. For example, a machine learning algorithm (deep learning algorithm) may be provided that has been trained on a corpus of example digital pathology images of a target condition, where the annotation has been performed by an expert.

In most cases, the exact value of the thresholds used in the algorithm will not significantly change the outcome of the pathology score. However, inaccuracies in the assessment of a pathology score can become a problem when the pathology score is closer to a clinical decision level, or if the given test is highly sensitive for one of the thresholds or parameters used in the image processing algorithm. A solution to these problems is now discussed.

The invention will first be broadly described according to the steps of the method of the third aspect and its optional embodiments.

The third aspect provides a method for digitally processing digital pathology image data to generate pathology score data, and a sensitivity analysis of the pathology score data comprising:
  a) obtaining 10 digital pathology image data comprising an image of a pathology sample;
  b) classifying 11 objects in the digital pathology image data into a plurality of candidate objects;
  c) assigning 12 a first pathological state to at least one candidate object in the plurality of candidate objects according to one or more detection thresholds and/or detection probabilities;
  d) obtaining 13 initial pathology score data of the pathology sample based on the candidate objects in the plurality of candidate objects having been assigned the first pathological state;
  e) perturbing 14 the one or more detection thresholds and/or the detection probabilities according to a perturbation function to generate a perturbed detection threshold and/or a perturbed detection probability;
  f) assigning 15 the first pathological state to at least one candidate object in the plurality of candidate objects according to the one or more perturbed detection thresholds and/or perturbed detection probabilities;
  g) obtaining 16 updated pathology score data of the pathology sample based on the candidate objects having been assigned the first pathological state according to the one or more perturbed detection thresholds and/or the perturbed detection probabilities, wherein a comparison of the initial pathology score data and the updated pathology score data defines a sensitivity of the pathology score data.

The skilled person will appreciate that the following algorithm is applied as a digital image processing algorithm implemented by a computer processor, for example.

In step a), the initial image data required for generating pathology score data and an associated sensitivity analysis is acquired. In a case where a sensitivity analysis of a digital pathology image is required close to the time of its acquisition, the digital pathology image may be acquired from a digital light microscope, or a digital fluorescence microscope as part of a digital pathology system, for example. In a case where a sensitivity analysis is to be performed on archived images, original digital pathology images stored in a PACS archive may be acquired from a PACS system via a computer network of a medical facility and transmitted to a PC terminal, a handheld computer, or another computer processing means, for example. Accordingly, the technique is applicable to archived digital pathology images as well as at the time of image acquisition.

An unprocessed digital pathology image contains visual representations of many objects such as cell nuclei, partial cell nuclei, cell membranes, cancer cells, fibroblasts, immune cells, and the like. For a certain immunohistological protocol, it is likely that a subset of these objects will be stained and analysed. In the specific example of the "PD-L1 IHC 22C3" test referenced earlier, it is generally necessary to identify viable tumour cells in the digital pathology image.

Optionally, a pre-processing step may be provided comprising smoothing the original digital pathology image to suppress noise. In the case of haematoxylin stain data, typically the pixels of the original digital pathology image obtained in step a) are also subjected to colour characterization to remove pixels having a colour component less than 10% of the full-scale intensity, for example. Of course, a colour characterization algorithm has configuration parameters that may be thresholded according to the present approach. Optionally, a morphological closing algorithm is subsequently applied to the smoothed and colour-characterized digital pathology image to correct for bright spots in the chromatin pattern.

In step b), there is accordingly a process of classifying objects in the digital pathology image data into candidate objects (which will be required in subsequent analysis) and other objects which are not required in the subsequent analysis. In the case of the "PD-L1 IHC 22C3" test, the candidate objects are viable tumour cells. Therefore, cytoplasmic staining artefacts, immune cells, normal cells, necrotic cells, and debris are excluded from the analysis.

Optionally, the classification process may be partially, or entirely performed according to a deep-learning approach. In such an approach, following the preprocessing of a whole slide image (digital pathology image data), various types of deep-learning approaches that can be applied to the present technique are broadly defined as supervised learning, unsupervised learning, semi-supervised learning, and multiple instance learning.

A deep learning algorithm comprises a cascade of layers taking the output of the previous layer as the input to a subsequent layer. The components in each layer are typically non-linear functions that perform the task of feature extraction, for example. Deep learning algorithms may comprise unsupervised and/or supervised learning stages. In a deep learning approach, critical parameters are typically thresholds on probability (output of a soft-max layer) or thresholds on derived uncertainty/confidence measure(s) in the output of the network.

Optionally, the classification process may be partially, or entirely performed using a supervised learning algorithm. Supervised learning techniques infer a function representing a mapping between items in the digital input image data to their appropriate labels (such as "T-cell"). Examples of a supervised learning algorithm are Convolutional Neural Networks (CNNs), or Support Vector Machines (SVM).

Optionally, the classification process may be partially, or entirely performed using an unsupervised learning algorithm. Unsupervised learning techniques infer a function describing hidden structures in unlabelled images. Examples of unsupervised learning approaches are principal component analysis and k-means analysis.

Optionally, the classification process may be partially, or entirely performed using a semi-supervised learning algorithm.

Optionally, the classification process may be partially, or entirely performed using a multiple instance learning algorithm.

The skilled person will appreciate that dependent upon the specific immunohistological protocol to be applied, other objects or combinations of objects may be identified. In the specific case of the "PD-L1 IHC 22C3" protocol, at least 100 candidate objects should be classified before generating test score, although for other pathology test protocols greater or fewer than 100 candidate objects may need to be identified.

Optionally, the technique to discover viable tumour cells and to assign them a status as candidate objects is to apply a morphological opening algorithm over the digital pathology image to remove small cells and fibroblasts. Then, a morphological closing algorithm is applied to expand neighbouring nuclei in the digital pathology image to form one object. Subsequently, a hole filling algorithm is applied in the tumour area to remove background areas. Finally, a further iteration of the morphological opening algorithm is applied to smooth the border of the tumour area, thus compensating for artefacts resulting from previous morphological algorithm operations.

Optionally, a wide range of image processing techniques can be used to perform the classification of objects in the digital pathology image data into candidate objects such as deep learning, segmentation, feature extraction, unsupervised learning, clustering, K-means, principal component analysis, or supervised learning approaches such as support vector machines or convolutional neural networks.

It is important to note that the image processing algorithms discussed in the foregoing paragraphs are configurable with a wide range of parameters. As a simple example, the optional pre-processing step may threshold pixels of a digital pathology image at intensity value of 10%, but instead a value of 5% or 15% could be chosen. There is a complex interaction between the thresholding value chosen and which objects in the digital pathology image may eventually be classified as candidate objects in step b) for example. The morphological algorithms and classification algorithms used for classifying objects in step b) also have a completed range of set of configuration parameters which affect the classification of the candidate objects.

FIG. 2a) illustrates a digital pathology image 20 in which a solid mask 22 has been used to indicate areas that belong to connective tissue or background areas which are therefore not viable tumour cells 24.

In step c), a first pathological state (histopathological state, cytopathological state) is assigned to one or more candidate objects in the plurality of candidate objects according to one or more detection thresholds and/or detection probabilities. Given the broad range of digital pathology tests that the present invention may be applied to, the assignment the first pathological state to a candidate object may be considered to be a small step in determining a subsequent diagnostic result. As a specific example, part of the "PD-L1 IHC 22C3" protocol is a requirement to count the number of viable tumour cells in a given area showing positive cell membrane staining for the PD-L1 biomarker. In this specific example, a candidate object is a viable tumour cell, and the assignment of a first pathological state is that the considered candid object is "positive for PD-L1 biomarker", or its equivalent digital representation. For example, over a given area of digital pathology image, the candidate objects could be represented in data structure by a column vector, with a logic "zero" representing no PD-L1 biomarker expression and a logic "one" representing PD-L1 biomarker expression. Alternatively, the data structure can comprise a column vector representing the relative proportion of PD-L1 biomarker expression.

In step d), an initial pathology score (or initial histopathology score, initial cytopathology score) on the pathology sample is generated. In the case of the specific "PD-L1 IHC 22C3" protocol currently being considered, this step comprises calculating the "tumour proportion score" as the initial pathology score which is the percentage of viable tumour cells (candidate objects) showing partial or complete membrane staining relative to all viable tumour cells present in the sample (positive and negative). However, the skilled person will appreciate that for a different protocol, different types of cell may be identified as candidate objects, and a different calculation may be made to obtain the initial pathology score.

Optionally, the initial pathology score may be displayed to a user by a graphical user interface (GUI) one of the technique to be discussed subsequently in relation to output methods.

Ordinarily, a user would be satisfied with the initial pathology score so obtained. However, as discussed in relation to steps b) and c), image processing and classification techniques are parameterisable, and small alterations in how the image processing and classification algorithms are parameterised can lead to changes in the pathology score.

Figure 3:
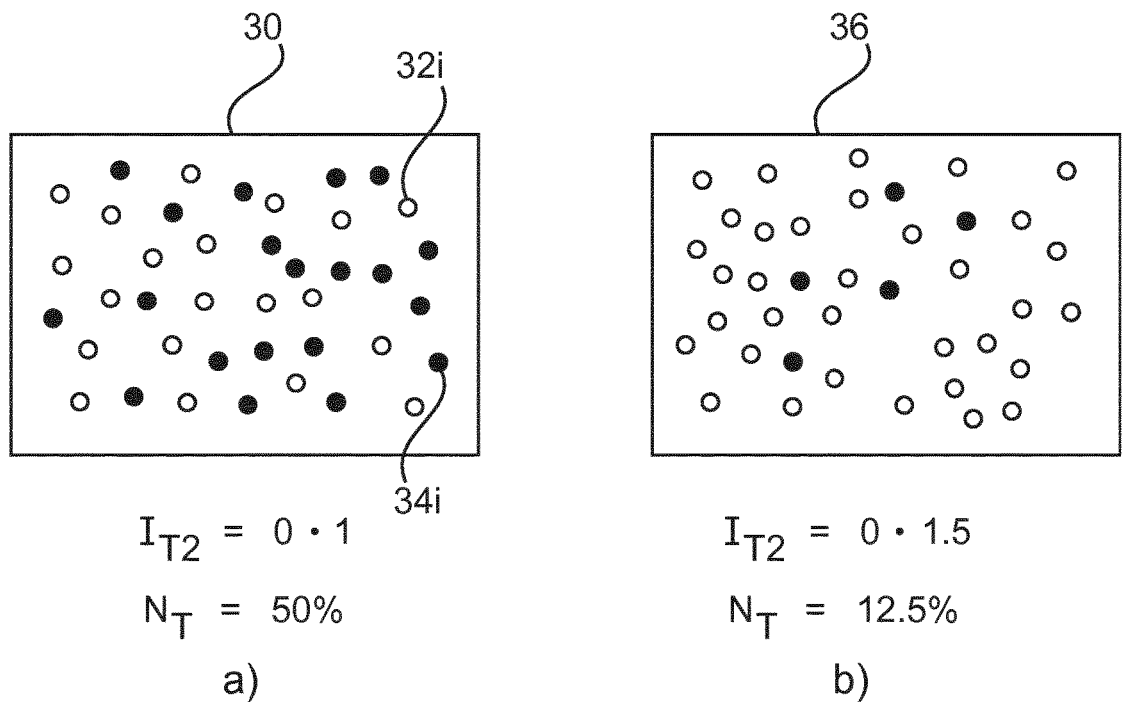
FIGS. 3a) and b) schematically demonstrate the effect of adjusting a detection threshold on detected candidate objects in digital pathology image data.

FIG. 3a) schematically illustrates a digital pathology image 30 which steps a), b), and c) have been applied. The hollow circles $32_i$ represent non-viable tumour cells (relative to the specific example) and the filled circles $34_i$ illustrate viable tumour cells. In digital pathology image 30, a preprocessing step thresholding the original digital pathology image to pixels having an intensity greater than $I_{T1}$=0.1 has been applied, resulting in around 50% of the identified objects in the image being classified as candidate objects (such as a viable tumour cell).

FIG. 3b) schematically illustrates a digital pathology image 36 in which a pre-processing step thresholding the original digital pathology image to pixels having an intensity greater than $I_{T2}$=0.15 has been applied. In this case, it appears that many viable tumour cells have been erroneously removed from the digital pathology image by the thresholding step resulting in around 12.5% of the identified objects in the image being classified as candidate objects (such as a viable tumour cell). This is an example of how a small change in an algorithm parameter can lead to a significant change (significant sensitivity) in a pathology result.

In step e), a perturbation is applied to a detection threshold and/or a detection probability according to a perturbation function. In other words, in the simple example considered in FIGS. 3a) and 3b), having calculated the initial pathology score data using a cut-off pixel intensity of $I_{T1}$=0.1, a perturbed detection threshold of $I_{T2}$=0.15 has been applied as the perturbed detection threshold. In this simple example, the perturbation function is thus a positive step function of 0.05.

Figure 4:
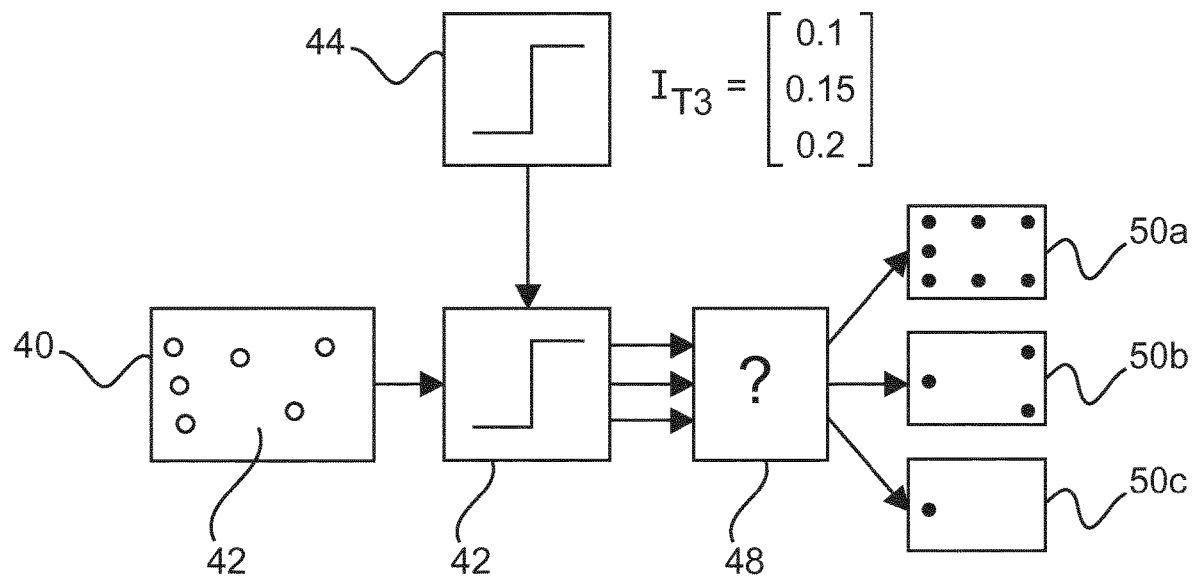
FIG. 4 schematically illustrates a simple digital pathology image analysis pipeline.

FIG. 4 illustrates the generation of a simple perturbation function for one variable (initial pixel thresholding) of a digital pathology image analysis pipeline.

A perturbation function generator 44 provides the column vector $I_{T3}$ comprising three values of an image level threshold. An initial digital pathology image 40 comprising objects which may or may not be classified as candidate objects 42 is input, and the thresholding function 46 is applied three times to generate three intermediate images generated at the three different threshold levels generated by the perturbation function. The three intermediate images are input to an image classifier 48 to yield digital pathology output images 50a, 50b, and 50c comprising differing numbers of candidate objects dependent upon the level of the perturbation function applied to the initial threshold.

Of course, the perturbation function generator 44 may generate the perturbation function in many different ways. The skilled person will appreciate that the output of the perturbation function would be scaled to a range of values appropriate to the stage in the analysis pipeline and the particular function to which the perturbation is applied. Optionally, the perturbation function generator 44 is configured to select the detection threshold and/or the detection probability randomly from a probability distribution, such as a Gaussian distribution, a uniform distribution, a chi-squared distribution, or the like. The perturbation function generator 44 may be configured to select the detection threshold from a pre-provided range of values, an algebraic function, a random number generator operating within a predetermined scaling, a chaotic attractor function, or the like.

A perturbation function may be based on historically obtained calibration and training data. For example, a population of pathologists could be used to classify test slides, and this would enable the derivation of realistic ranges of perturbation values from the variations observed in the results from the population of pathologists. The derived realistic ranges could then be provided as the perturbation function.

In step f), there is provided the step of reassigning the first pathological state to one or more candidate objects in the plurality of candidate objects, or to at least one candidate object in a perturbed plurality of candidate objects, according to the one or more perturbed detection thresholds and/or perturbed detection probabilities.

With a perturbed detection threshold, the first pathological state may be used to detect a smaller or greater number of candidate objects in the plurality of candidate objects, dependent on the amplitude of the perturbation and the sensitivity of the analysis pipeline to that perturbation. Optionally, parameters applied in the pre-processing and/or classification steps are perturbed, meaning that a perturbed plurality of candidate objects is generated. In other words, referring to the specific example of PD-L1 biomarker detection, perturbation of algorithms applied in steps a) and b) may lead to some objects originally included in the plurality of candidate objects to be excluded from the perturbed plurality of candidate objects, and vice versa. Subsequently, algorithms used to assign a first pathological state to one or more viable tumour cells (candidate objects) may be sensitive to a variation in the detection thresholds and/or detection abilities as well.

In step g), an updated pathology score of the pathology (histopathlogy, cytopathology) sample is provided based upon the changed number of candidate objects having been assigned the first pathological state. Because the updated pathology score has been calculated according to a perturbed section threshold and/or probability, it is likely that it will be slightly (or significantly) different to the initial pathology score. Accordingly, a comparison between the initial pathology score data and the updated pathology score data defines a sensitivity of pathology score data obtained using a particular analysis pipeline.

Optionally, the detection threshold and/or detection probability may be considered a detection condition.

FIGS. 2b-2d) illustrate results of the specific example of the use of the PD-L1 biomarker (negative and positive expression) in determining the Tumour Proportion Score (TPS) present in digital pathology image slide 20. A grey shaded area indicated as 26b, 26c, and 26d respectively shows areas with overexpression of the PD-L1 biomarker for three different intensity thresholds.

In FIG. 2b), a pixel intensity threshold at 0.1 is applied, resulting in an overall TPS of 33%.

In FIG. 2c), a pixel intensity threshold of 0.15 is applied, resulting in an overall TPS of 5%.

Figure 2:
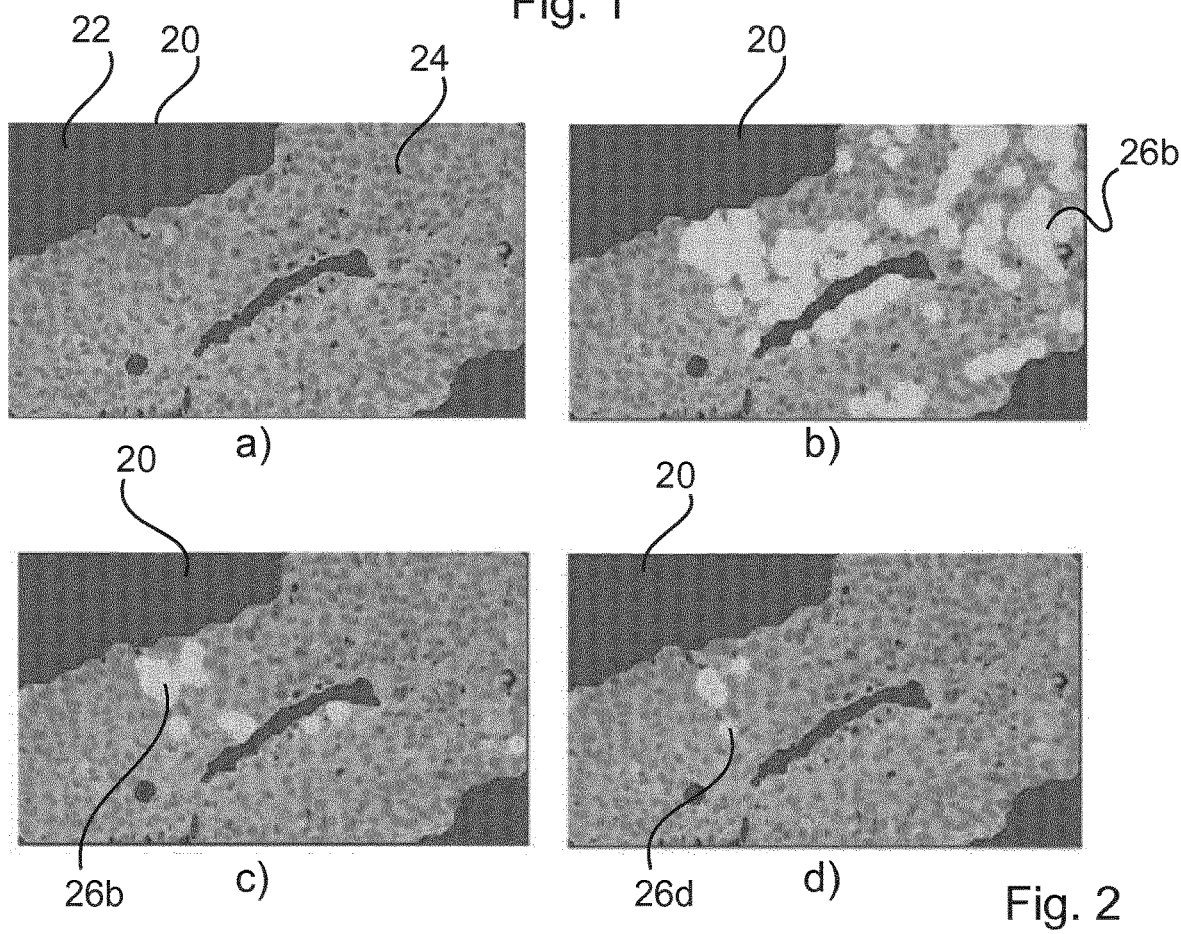
FIGS. 2a) to d) schematically shows the effect of the variation of an algorithm parameter on a digital image analysis pipeline.

In FIG. 2d), a pixel intensity threshold of 0.2 is applied, resulting in an overall TPS of 1%. Notably, a TPS of 1% is the boundary for a condition in which no PD-L1 expression occurs, representing a critical clinical decision boundary for treatment with certain compounds. Therefore, the sensitivity analysis and variable TPS scores represented by the illustrations of FIG. 2 may automatically provide results that enable a medical professional to more accurately and confidently assess the sensitivity of a digital pathology score in a clinical context.

Although many references have been made to the specific test of the Dako™ PD-L1 biomarker, it will be appreciated by a skilled person that this specific test involves a complicated assessment of positive and negative biomarker expression. The sensitivity analysis of digital pathological image data to perturbations of internal analysis pipeline parameters may also be performed for simpler pathological, histopathological, or cytopathological approaches.

Optionally, the one or more detection thresholds are associated with testing the sensitivity of a "PD-L1" pathology score.

For example, the "CD3" test is often used as a marker of T-cells to classify lymphomas.

After obtaining digital pathology image data of a sample according to the CD3 protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself. Then, the image is segmented into different tissue areas of interest which contain tumour cells, the objects of interest, by one or more critical detection thresholds (parameters). Following this segmentation procedure, a differentiation may be made between different amounts of staining (expression levels) in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, CD3 staining accounts for i) intratumoural lymphocytes which are lymphocytes located in the stroma of the tumour mass or inside the tumour cell nests and ii) peri-tumoral lymphocytes which are lymphocytes surrounding the tumour mass. For the lymphocytes, a distribution and density score is applied. Scores ranged from 0 to 6. The lymphocyte distribution score, which ranges from 0 to 3, is defined as follows: 0=absence of lymphocytes within the tissue, 1=presence of lymphocytes occupying <25% of the tissue, 2=presence of lymphocytes occupying 25 to 50% of the tissue, and 3=presence of lymphocytes occupying >50% of tissue. Lymphocyte density, which ranges from 0 to 3, is defined as follows: 0=absent, 1=mild, 2=moderate, and 3=severe.

This acquired data can be used for sensitivity analysis, the parameters of the algorithm used to segment and/or identify lymphocytes being one detection threshold (parameter) that is suitable for perturbation according to the algorithm described. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "CD3" pathology score.

For example, the "CD8" protocol can be used to identify effector T-cells in the tumour tissue.

After obtaining digital pathology image data of a sample according to the CD8 protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is digitally segmented into different tissue areas of interest which contain tumour cells, the objects of interest, by one or more critical threshold parameters. Following this segmentation procedure, a digital differentiation is made between different concentrations of stain (expression levels) in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, CD8 staining accounts for i) intratumoural lymphocytes which are lymphocytes located in the stroma of the tumour mass or inside the tumour cell nests and ii) peritumoural lymphocytes which lymphocytes surround a tumour mass. A factor that affects the lymphocyte distribution and density scores is how precisely stromal areas are segmented, for example, and/or the detection thresholds for CD8 positive calling, and/or the thresholds for nucleus detection. Scores range from 0 to 6. The lymphocyte distribution score, which ranges from 0 to 3, is defined as follows: 0=absence of lymphocytes within the tissue, 1=presence of lymphocytes occupying <25% of the tissue, 2=presence of lymphocytes occupying 25 to 50% of the tissue, and 3=presence of lymphocytes occupying >50% of tissue. Lymphocyte density, which ranges from 0 to 3, is defined as follows: 0=absent, 1=mild, 2=moderate, and 3=severe.

This acquired data can be used for sensitivity analysis according to the algorithm described in this application, with the criterion for the assignment of the first and second pathological states being an example of one threshold (parameter) suitable for perturbation. By comparing the different areas of the tumour and its surrounding tissue, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "CD8" pathology score.

For example, the "ER" protocol (Oestrogen Receptor) is often used in association with mammography screening programmes. After obtaining digital pathology image data of a sample according to the ER protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is segmented into different tissue areas of interest which contain tumour cells, the objects of interest, by one or more critical threshold parameters. Following this segmentation procedure, a digital differentiation between different expression levels in the tumour tissue, comprising tumour cells, the objects of interest is made. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, a total score (TS) is the sum of the proportion score (PS) and the intensity score (IS), ranging from 0; 2-8. A positive result for both ER and PR is defined as TS≥3. A proportion score (PS) is assigned representing the proportion of tumour cells with positive nuclear staining. The PS ranges from 0 to 5, where 0=0, 1=0-$\frac{1}{100}$, 2=>$\frac{1}{100}$-$\frac{1}{10}$, 3=>$\frac{1}{10}$ to $\frac{1}{3}$, 4=>$\frac{1}{3}$ to $\frac{2}{3}$ and 5=>$\frac{2}{3}$ to 1. An intensity score (IS) is assigned representing the average staining intensity of all positive tumour cells. The IS ranges from 0 to 3, where 0=negative, 1=weak, 2=intermediate and 3=strong. Frequently, ER and PR analysis are combined in one diagnostic test.

This acquired data can be used for sensitivity analysis, the proportion score being an example of one threshold (parameter) suitable for perturbation according to the algorithm described herein and the intensity score being an example of another threshold (parameter) suitable for perturbation. By comparing the different areas of the tumour, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "ER" pathology score.

After obtaining digital pathology image data of a sample according to the PR protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is segmented into different tissue areas of interest which contain tumour cells, the objects of interest, by one or more critical threshold parameters. Following this segmentation procedure, a differentiation is made between different expression levels in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, a total score (TS) is the sum of the proportion score (PS) and the intensity score (IS), ranging from 0; 2-8. A positive result for both ER and PR is defined as TS≥3. A proportion score (PS) is assigned representing the proportion of tumour cells with positive nuclear staining. The PS ranges from 0 to 5, where 0=0, 1=0-$\frac{1}{100}$, 2=>$\frac{1}{100}$-$\frac{1}{10}$, 3=>$\frac{1}{10}$ to $\frac{1}{3}$, 4=>$\frac{1}{3}$ to $\frac{2}{3}$ and 5=>$\frac{2}{3}$ to 1. An intensity score (IS) is assigned representing the average staining intensity of all positive tumour cells. The IS ranges from 0 to 3, where 0=negative, 1=weak, 2=intermediate and 3=strong. Frequently, ER and PR analysis are combined in one diagnostic test.

This acquired data can be used for sensitivity analysis according to the algorithm described in this application. For example, the proportion score is one threshold (parameter) suitable for perturbation and the intensity score is an example of another parameter suitable for perturbation. By comparing the different areas of the tumour, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "PR" pathology score.

For example, the "HER2" protocol (Herceptin) is used to detect the presence of abnormal levels of Herceptin in mammary tissue, a predictive biomarker for breast cancer.

After obtaining digital pathology image data of a sample according to the HER2 protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is segmented into different tissue areas of interest which contain tumour cells, the objects of interest, by one or more critical threshold parameters. Following this segmentation procedure, it is differentiated between different expression levels in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, HER2-negative tumours (score 0) harbour membranous HER2 expression <10% of the tumour cells. A score of +1 corresponds to membranous HER2 expression in >10% of tumour cells, while a score of +2 corresponds to tumour cells with a weak to moderate HER2 expression in the membrane of >10% of tumour cells. A strong complete membrane staining in >10% of tumour cells corresponds to a score of +3. This acquired data can be used for sensitivity analysis according to the algorithm of this application, the membranous, i.e. spatial information being an example of one threshold (parameter) for perturbation and the intensity score being an example of another parameter suitable for perturbation. By comparing the different areas of the tumour, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "HER2" pathology score.

For example, the "EGFR" protocol (Epidermal growth factor receptor) test can be used to test for cell mutations that lead to EGFR over-expression, which has been associated with a number of cancers.

After obtaining digital pathology image data of a sample according to the EGFR protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is segmented into different tissue areas of interest which contain tumour cells, the objects of interest, by one or more critical threshold parameters. Following this segmentation procedure, it is differentiated between different expression levels in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area.

In this example, EGFR expression of preferably colorectal tumours is evaluated as the following: EGFR-negative tumours do not possess membranous staining above background in all tumour cells. Contrarily, EGFR-positive staining and therefore, expression is defined as any IHC staining of tumour cell membranes above background level; whether it is complete or incomplete circumferential staining. The staining intensity and hence, expression is a score of +1, +2 or +3, where more than 0% of tumour cells are stained and therefore, positive for EGFR. This acquired data can be used for sensitivity analysis according to the algorithm described in this application, the intensity score being the threshold (parameter) for perturbation. By comparing the different areas of the tumour, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "EGFR" pathology score.

For example, the "Ki67" protocol detects the Ki7 antigen. After following the standard procedure to obtain digital pathology of a sample prepared according to the "Ki67" protocol.

After obtaining digital pathology image data of a sample according to the Ki67 protocol, using, for example, a digital light microscope to capture the stained sections, package, digital pathology image data of the sample at different magnifications is obtained (4×, 10×, 20×, 40×) either using a software imaging package, or a plurality of digital pathology images at different magnifications may be captured by the digital light microscope itself.

Then, the image is segmented into different tissue areas of interest which contain tumour cells, the objects of interest, by one or more critical threshold parameters. Following this segmentation procedure, it is differentiated between different expression levels in the tumour tissue, comprising tumour cells, the objects of interest. This difference between different areas of the same tumour is known as tumour heterogeneity. Hence, a specific expression pattern or first pathological state is assigned to certain areas of the tumour tissue, while another expression pattern and second pathological state can be assigned to another area of the tumour tissue and even another expression pattern and at least pathological state can be assigned to another area. There are different approaches to obtain the Ki67 score. One method involves selecting five different areas of the tumour, where 100 tumour cells in every area are evaluated. The percentage of positive Ki67 cells (stained nuclei) out of 100 cells is taken into account and the results of the five areas are summed up.

This acquired data can be used for sensitivity analysis, the spatial information, i.e. nuclear staining being the threshold (parameter) undergoing perturbation. By comparing the different areas of the tumour, therefore obtaining different threshold values, one threshold value is defined. Moreover, the defined detection threshold can be adjusted manually, too. This definition aids the pathologist during the evaluation of the tissue to prove whether the evaluation of the tissue is reasonable and within an objectively-defined range.

Optionally, the one or more detection thresholds are associated with testing the sensitivity of a "Ki67" pathology score.

Optionally, the one or more detection thresholds and/or detection probabilities represent a variation in automatic morphological feature detection when determining the presence of a candidate object in the digital pathology image data.

Optionally, the one or more detection thresholds represent a probability of automatic classification of the objects in the digital pathology image data into the plurality of candidate objects.

Optionally, the detection threshold and/or the detection probability characterise an intensity level and/or a wavelength range of light emitted from a pathology sample and represented in the digital pathology image data.

Optionally, the intensity level and/or the wavelength range emitted from the pathology sample and represented in the digital pathology image data indicate a relative level of the expression of a biomarker.

Optionally, the method further comprises:
f1) repeating steps c) to g) to obtain a plurality of perturbed detection thresholds and/or perturbed detection probabilities forming a sensitivity function of the pathology score of the digital pathology image data;
f2) optionally, computing a relative detection threshold change necessary to provide a change in the pathology score.

Optionally, the method further comprises:
d1) data by counting the number of candidate objects in a field of interest of the digital pathology data having been assigned the first pathological state before and/or after perturbation, or by calculating a percentage score of the number of candidate objects in a field of interest of the digital pathology data having been assigned the first pathological state before and/or after perturbation.

Figure 5:
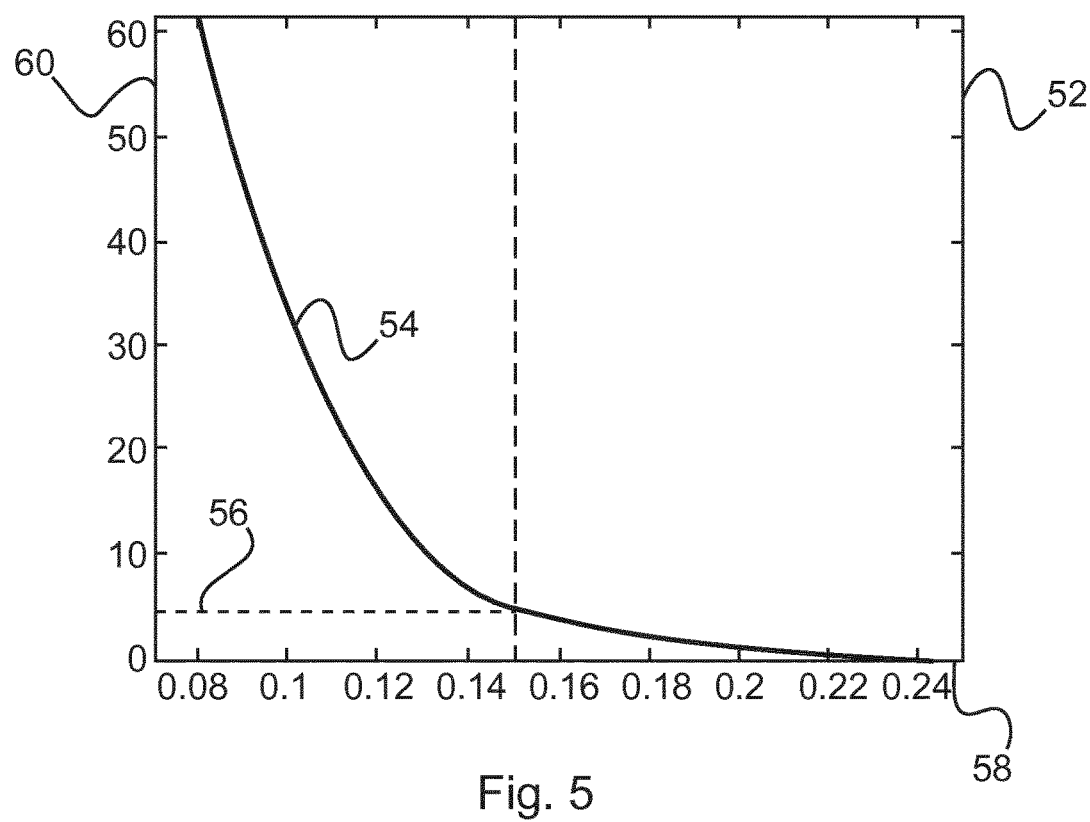
FIG. 5 shows an example plot of the tumour proportion score as a function of the threshold on DAB absorption.

FIG. 5 illustrates a plot 52 showing a specific example of a sensitivity function 54 of the Tumour Proportion Score (TPS) obtained using the "PD-L1 IHC 22C3". The X-axis represents the threshold value for the assessment of the presence of the PD-L1 stain. In other words, the X-axis 58 represents a range of potential perturbation values. The Y-axis 60 represents the percentage value of the TPS. For a particular clinical protocol, an optimum value of the pathology score data (in this case the dotted line 56 representing an X-axis TPS intercept at 5%) may be provided. In this case, a threshold value of PD-L1 intensity at 0.15 provides a updated pathology score close to this clinical threshold.

Many simple examples discussed above involve detecting for the positive expression of a single biomarker. However, the "PD-L1 IHC" requires detecting for the positive and the negative expression of the PD-L1 biomarker. The following embodiment addresses this case:

Optionally, the method further comprises:
c1) assigning a second pathological state to at least one candidate object showing positive expression of a first biomarker of interest;
c2) assigning a third pathological state to at least one candidate object showing negative expression of a first biomarker of interest, and
d2) obtaining the initial pathology score data by performing a calculation using the candidate objects in the field of interest of the digital pathology data in the second and third pathological states;
e1) perturbing the detection thresholds used to assign the second and third pathological states to the candidate objects;
e2) reassigning the second and third pathological states to the candidate objects after perturbation; and
g1) obtaining updated pathology score data by performing a calculation using the candidate objects in the second and third pathological states after perturbation.

Optionally, multi-biomarker imaging may be supported by this technique. In other words, in step c3) a second pathological state may be assigned to at least one candidate object showing positive expression of a second biomarker of interest. In step c4), a third pathological state may be assigned to at least one candidate showing positive expression of a third biomarker of interest. Optionally, the first, second, and third biomarkers are immunofluorescence biomarkers.

An immunohistochemistry example of more complicated analysis pipeline relating to the derivation of the TPS (tumour proportion score) in PD-L1 stained tissue comprises optional steps of:
1) Obtaining an IHC stained histopathology image at relatively high magnification (typically at 10×, 20×, or 40×).
2) Applying an algorithm that (semi-) automatically segments the image into objects of interest, using one or more critical threshold parameters.
3) Applying an algorithm that (semi-) automatically differentiates between normal expression and overexpression in the objects of interest, using one or more critical thresholds or parameter settings.
4) Performing a sensitivity analysis as described in this application.

5) Providing visual feedback or warning message if the sensitivity analysis indicates that the score may change from one decision level to another as a result of the practical variation in the critical thresholds.
6) Providing visual feedback of areas of the digital pathology image data that are most sensitive to threshold variation.
7) Providing visual feedback of the areas that did not meet the criteria for scoring.

In one or more of steps 2), 3), and/or 4), a deep-learning or machine-learning approach may optionally be applied.

Accordingly, given an initial RGB image of PD-L1 stained tissue, colour deconvolution may be performed to separate the absorption of haematoxylin from the absorption of the DAB marker using a method as discussed in the paper "A Method for Normalizing Histology Slides for Quantitative Analysis" by Macenko, et al." referenced in the "Background" section above.

The location of nuclei in the deconvolved image is obtained by the following steps:
8) Smoothing of the haematoxylin stain data (in order to suppress noise) and thresholding at absorption level 0.1.
9) Applying morphological closing to correct the bright spots in the chromatin pattern.
10) Applying morphological opening to remove small cells and fibroblasts.
11) Applying morphological closing to grow neighbouring nuclei together to form one object.
12) Applying hole filling to the tumour area and removing background areas.
13) performing a final morphological opening to smoothen the border of the tumour area to compensate artefacts that resulted from previous morphological operations.

In this case, the nominator of the TPS is obtained after thresholding the DAB (PD-L1) stain absorption data. DAB absorption (within the area with viable tumour cells) above a certain threshold value indicates the area with overexpression, in other words, the PD-L1 tumour cells. As previously referenced in FIGS. 2b) to 2d), these images are sensitive to the perturbations in threshold parameters in the analysis pipeline.

FIG. 5 illustrates the TPS as a function (y-axis) of perturbation of the detection threshold on DAB absorption (x-axis). The "optimal threshold" for assessment of the PD-L1 stain in the case of FIG. 5 is indicated by the vertical dashed line. A detection threshold value 0.05 lower would have included more tumour cells, resulting in a significantly higher estimate of the TPS. A detection threshold 0.05 higher would have included many fewer tumour cells causing the TPS to drop to the critical clinical decision level of 1%.

Figure 6:
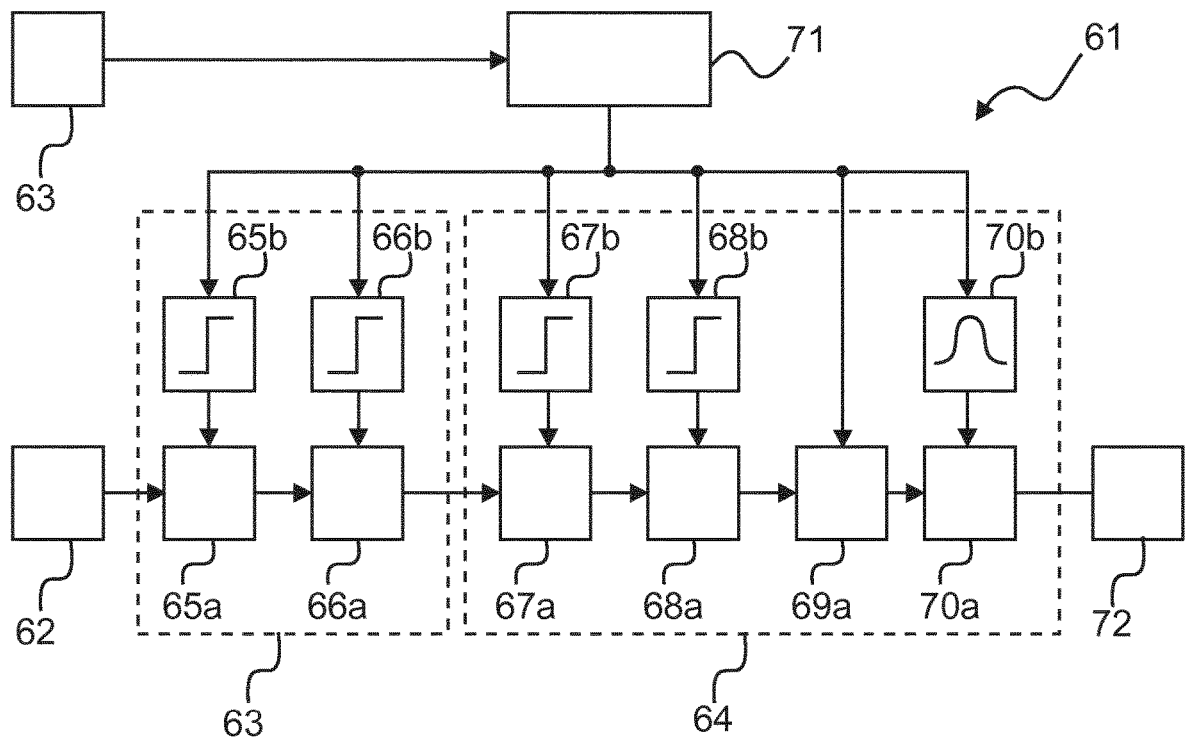
FIG. 6 schematically illustrates a complicated digital pathology image analysis pipeline.

FIG. 6 illustrates an example of a complicated analysis pipeline 61 for implementation of the specific example given above.

A digital pathology image data input unit 62 receives and pre-processes digital pathology image data. A user provides perturbation configuration data 63 (for example, via a input graphical user interface on a digital pathology system and/or image analysis software). The analysis pipeline in this particular example is divided into a nuclei location determiner 63 and a tumour cell identifier 64.

In the nuclei location determiner 63 a preparation unit 64a smooths haematoxylin stain data (to suppress noise) and thresholds at a given absorption level. A first morphological closing unit 66a corrects for bright spots in the chromatin pattern.

In the tumour cell identifier 64 a morphological opening unit 67a is configured to remove images of small cells and fibroblasts in the digital pathology image. A morphological closing unit 68a is configured to grow neighbouring nuclei together to form one object. A hole filling unit 69a is configured to apply hole filling to the tumour area and remove background areas recognised by the low absorption value. A morphological opening unit 70a is applied to smoothen the border of the tumour area to thus compensate artefacts resulting from previous morphological operations.

In the analysis pipeline, each processing sub-unit 65a to 70a is connected to a respective perturbation determination units 65b to 70b. In the specific example, perturbation unit 70b selects perturbation values of a morphological closing algorithm based on a Gaussian distribution. The rest of the perturbation units provide perturbation values based on a step function. Perturbation control unit 71 receives the perturbation configuration data 63 input by the user and determines a perturbation specification likely to give sufficient coverage over the total search space of perturbation options. Having determined the perturbation specification, perturbation settings for each of the perturbation units are calculated and transmitted to the perturbation units 65b to 70b. Of course, not all steps of an analysis pipeline need be characterized by adjustable detection thresholds and/or probabilities, and one or more settings of the analysis pipeline may be "hard-coded" or fixed, without being subject to perturbation.

The perturbation control unit 71 may, for reasons of computational simplicity, operate a "one at a time" sensitivity analysis protocol in which one or more of the perturbation units 65b to 70b is adjusted at a time, with the other perturbation units being held at a constant perturbation value.

Optionally, the perturbation control unit 71 may apply a "random sampling" sensitivity analysis protocol in which one or more of the perturbation units 65b to 70b are addressed with randomly generated perturbation values (optionally within fixed boundary ranges). In this way, a large sample space of perturbation values may be sampled in a computationally efficient way, and also cross-correlations between perturbation settings of the perturbation units 65b to 70b may be assessed in a way that is not possible with a "one at a time" sensitivity analysis protocol.

Optionally, the perturbation control unit 71 may apply a "brute force" sensitivity analysis protocol in which one or more of the perturbation units 65b to 70b are addressed all combinations of their respective perturbation thresholds. This has the advantage that the sensitivity analysis is exhaustive, although may occupy so much computational time that the technique can only be applied with a powerful computer, or a simple analysis pipeline.

Optionally, the perturbation control unit 71 may apply a "gradient descent" algorithm, or another optimisation algorithm, to compute an optimal sensitivity.

Result collection unit 72 obtains and saves the pathology scores generated by the application of various combinations of perturbation setting to the analysis pipeline for the same input digital pathology image.

In an example, the tumour proportion score may be calculated as the number of PD-L1 positive tumour cells present in a plurality of candidate objects divided by the total number of PD-L1 positive and PD-L1 negative tumour cells present in a plurality of candidate objects (viable tumour cells).

The tumour proportion score may be used to differentiate between the three levels of no PD-L1 expression (partial or complete cell membrane staining in less than 1% of viable tumour cells), PD-L1 expression (partial or complete cell membrane staining in between 1 and 49% of viable tumour cells), and high PD-L1 expression (partial or complete cell membrane staining in greater than or equal to 50% of viable tumour cells).

Accordingly, a perturbation of detection thresholds and/or detection abilities used in the analysis pipeline can provide a medical professional with warning that a pathology protocol is so sensitive that it could affect the overall treatment indication.

Optionally, the method further comprises:
h1) outputting the sensitivity of the pathology score data to a user, optionally in combination with the initial and/or updated pathology score data and/or outputting the sensitivity of the pathology score relative to a clinical threshold.

Accordingly, the sensitivity of the pathology score data may be displayed on a graphical user interface (GUI) of a digital pathology system, or digital pathology software used on a personal computer (PC) or other digital display device. The pathology score data may be reported to a user as a numerical string, or as a colour map or heat map, for example. This provides the user of a digital pathology system and/or analysis software with immediate and intuitive feedback about the sensitivity of a given result in context with the original digital pathology slide image.

Optionally, the method further comprises:
b2) sub-sampling the digital pathology image data into a plurality of sectors;
g2) obtaining initial pathology score data and updated pathology score for each sector;
h2) generating a spatial sensitivity mask of the digital pathology image data; and
h3) displaying the spatial sensitivity mask to a user, optionally as a semi-transparent overlay in alignment with the digital pathology image data.

Figure 7:
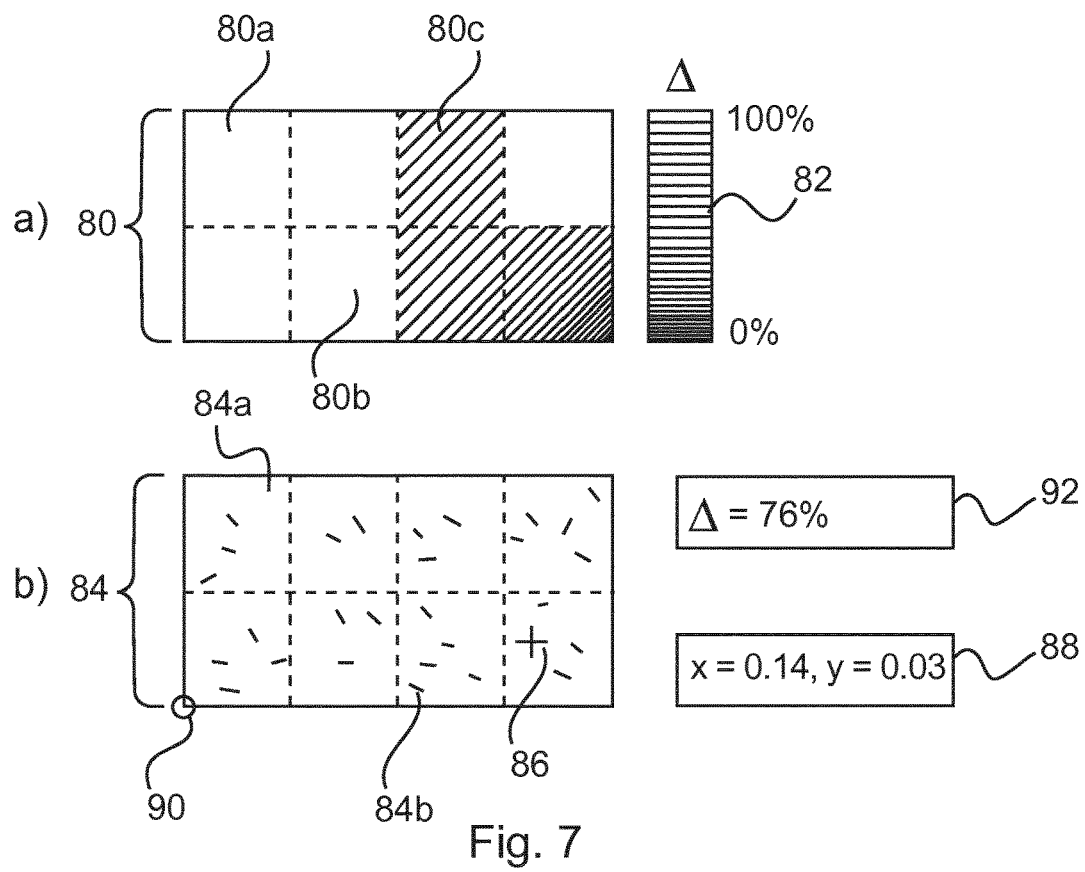
FIGS. 7a) and b) schematically illustrate examples of output displays of digital pathology image data sensitivity information.

FIG. 7a) illustrates a possible display format in which the digital pathology image data 80 has been divided into a plurality of sub-sectors 80a, 80b, 80c . . . . In this display embodiment, an initial pathology score, an updated pathology score, and an overall sensitivity for each sub-sector has been calculated. A display legend 82 provides a guide to interpretation of the GUI. Saturated sub-sectors represent a low sensitivity to perturbation in the analysis pipeline, and non-saturated sub-sectors represent a high-sensitivity to perturbation in the analysis pipeline.

FIG. 7b) illustrates another possible display format in which the digital pathology image data 84 has been divided into sub-sectors 84a, 84b, . . . . In this display embodiment, an initial pathology score, an updated pathology score, and an overall sensitivity for each sub-sector has been calculated. In this GUI format, a user may move a mouse cursor 86 around the displayed digital pathology image data 84. An optional dialogue box 88 reports the current spatial position of the cursor in relation to the origin 90 of the displayed digital pathology image data 84. A sensitivity feedback dialogue box displays the calculated sensitivity of the pathology score at the location of the mouse cursor.

Optionally, a message may be provided to a user in an output step that indicates the sensitivity of the analysis. As an example, a calculation of the relative thresholds change necessary for relative change in score may be provided. Optionally, the required threshold change that would result in a different diagnostic result may be provided.

Optionally, the pathology sample is a histopathology sample or a cytopathology sample.

Figure 8:
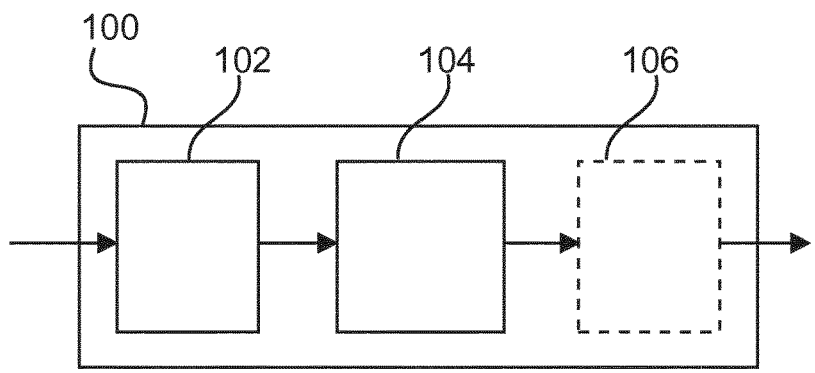
FIG. 8 schematically illustrates an apparatus in accordance with a first aspect.

FIG. 8 illustrates an apparatus 100 according to the first aspect.

According to the first aspect, there is provided an apparatus 100 for digitally processing digital pathology image data to generate pathology score data, and a sensitivity analysis of the pathology score data. The apparatus 100 comprises:
an input unit 102; and
a processing unit 104.

The input unit 102 is configured to obtain digital pathology image data comprising an image of a pathology sample.

The processing unit 104 is configured to classify objects in the digital pathology image data into a plurality of candidate objects, to assign a first pathological state to at least one candidate object in the plurality of candidate objects according to one or more detection thresholds and/or detection probabilities, to obtain initial pathology score data of the pathology sample based on the candidate objects in the plurality of candidate objects having been assigned the first pathological state, to perturb the one or more detection thresholds and/or the detection probabilities according to a perturbation function to generate a perturbed detection threshold and/or a perturbed detection probability, to reassign the first pathological state to at least one candidate object in the plurality of candidate objects, or to at least one candidate object in a perturbed plurality of candidate objects, according to the one or more perturbed detection thresholds and/or perturbed detection probabilities, to obtain updated pathology score data of the pathology sample based on the candidate objects having been reassigned the first pathological state according to the one or more perturbed detection thresholds and/or the perturbed detection probabilities, and to compare the initial pathology score data and the updated pathology score data to obtain a sensitivity of the pathology score data.

The apparatus may further comprise an output unit 106.

The input unit 102 may comprise a data communications modem capable of transferring digital pathology image data, for example a USB™ connection, a FireWire™ connection, a DICOM connection, and the like. Input unit 102 may comprise a hard disk drive and/or a removable hard disk drive, a USB drive, a DVD drive, or another means of transferring stored data. Data may be received over a secure communication network such as a LAN or WAN, or a secure wireless means.

It will be appreciated that the processing unit 102 may be practically implemented as any data processor capable of processing image data. For example, the apparatus 100 can be implemented on a personal computer, a smart phone processor, an embedded processor, a digital signal processor (DSP) or a processing unit instantiated on a field programmable gate array (FPGA). Optionally, part or all of the functions performed by the processing unit 100 may be performed using the acceleration capabilities available using a graphical processing unit GPU.

The output unit 106 may be provided with a similar range of modalities as discussed in respect of the input unit 102 in the case that the data output is raw data to be interpreted by another component. The output unit 16 may also comprise a graphics interface to display the results of a sensitivity analysis on a graphical user interface (GUI).

Figure 9:
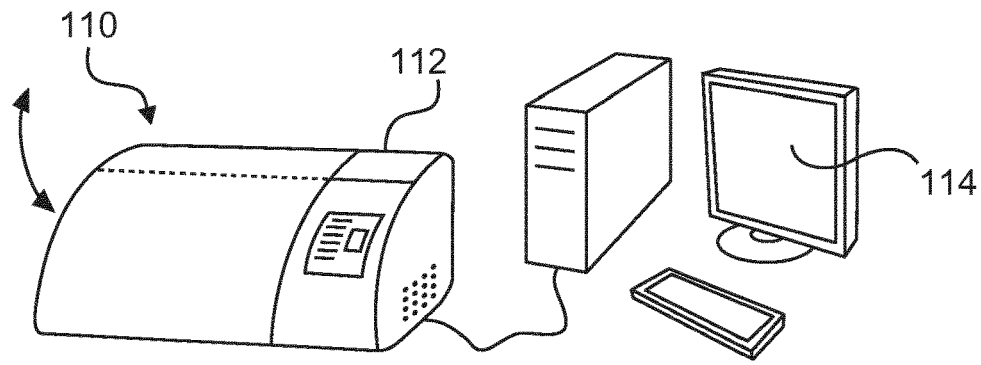
FIG. 9 schematically illustrates a digital pathology system in accordance with a second aspect.

FIG. 9 illustrates a digital pathology system 110.

According to a second aspect, there is provided a digital pathology system 110. The digital pathology system 110 comprises:
- a digital pathology image acquisition device 112; and
- an apparatus 114 according to the first aspect or one of its embodiments.

wherein the digital pathology image acquisition device 112 is configured to acquire digital pathology image data, and to communicate the digital pathology image data to the apparatus 114.

A computer program element may be stored on a computer unit, which might also be an embodiment of the present invention. This computing unit may be adapted to perform or induce performance of the steps of the method described above. Moreover, it may be adapted to operate the components of the above-described apparatus. The computing unit can be adapted to operate automatically and/or to execute orders of a user. A computer program may be loaded into a working memory of a data processor. The data processor may thus be equipped to carry out the method of the invention.

This exemplary embodiment of the invention covers both the computer program that has the intervention installed from the beginning, and a computer program that by means of an update turns an existing program into a program that uses the invention.

Optionally, the slide image data could be uploaded to a "PACS" system or local hospital server over a Local Area Network. Of course, the slide images could be saved on physical media such as a Digital Versatile Disk (DVD), a tape drive, or a USB stick and physically sent to a location hosting the server, where the physical media could be loaded onto the server.

Then, the slide image data are processed according to the second aspect, or its optional embodiments. The multi-view data of the field of view of the biological sample is then transmitted to a client device for use, for example by a graphical user interface capable of interpreting the multi-view data. Optionally, the multi-view data is interpreted into a display format (such as .JPG, .GIF, or another imaging format) on the server, and the GUI display of the multi-view data is transmitted to the client (an example of a "web-based application").

A computer program may be stored and/or distributed on a suitable medium, such as optical storage media, or a solid state medium supplied together with, or as a part of other hardware, but may also be distributed in other forms, such as via the Internet or other wired or wireless telecommunication systems. However, the computer program may also be presented over a network like the World Wide Web, and can also be downloaded into the working memory of a data processor from such a network. The image processing method according to the second aspect would then be performed on the According to a further exemplary embodiment of the present invention, a medium for making a computer program element available for downloading is provided, which computer program element is arranged to perform a method according to one of the previously described embodiments of the invention.

It should to be noted that embodiments of the invention are described with reference to different subject-matters. In particular, some embodiments are described with reference to method-type claims, whereas other embodiments are described with reference to device-type claims. However, a person skilled in the art will gather from the above, and the following description that, unless otherwise notified, in addition to any combination of features belonging to one type of subject-matter, also other combinations between features relating to different subject-matters is considered to be disclosed with this application.

All features can be combined to provide a synergetic effect that is more than the simple summation of the features. While the invention has been illustrated and described in detail in the drawings and foregoing description, such illustration and description are to be considered illustrative or exemplary, and not restrictive. The invention is not limited to the disclosed embodiments.

Other variations to the disclosed embodiments can be understood, and effected by those skilled in the art in practicing the claimed invention, from a study of the drawings, the disclosure, and the dependent claims.

In the claims, the word "comprising" does not exclude other elements or steps, and the indefinite article "a" or "an" does not exclude a plurality. A single processor, or other unit, may fulfil the functions of several items recited in the claims. The mere fact that certain measures are recited in mutually different dependent claims does not indicate that a combination of these measures cannot be used to advantage. Any reference signs in the claims should not be construed as limiting the scope.

The invention claimed is:

1. An apparatus for digitally processing digital pathology image data to generate pathology score data, and a sensitivity analysis of the pathology score data, wherein the sensitivity analysis means an assessment of how the pathology score data are affected by perturbations to parameters used in the determination or generation of the pathology score data, the apparatus comprising:
   an input unit; and
   a processing unit;
   wherein the input unit is configured to obtain digital pathology image data comprising an image of a pathology sample; and
   wherein the processing unit is configured:
   to classify objects in the digital pathology image data into a plurality of candidate objects, to assign a first pathological state to at least one candidate object in the plurality of candidate objects according to one or more detection thresholds and/or detection probabilities, wherein automatic morphological feature detection is utilized to identify the candidate objects;
   to obtain initial pathology score data of the pathology sample based on the candidate objects in the plurality of candidate objects having been assigned the first pathological state;
   to perturb the one or more detection thresholds and/or the detection probabilities according to a perturbation function to generate a perturbed detection threshold and/or a perturbed detection probability, wherein the perturbation function is configured to generate the perturbed detection threshold and/or the perturbed detection probability comprising selection utilizing a step function, random selection utilizing a probability distribution, selection utilizing a pre-provided range of values, selection utilizing an algebraic function, selection utilizing a random number generator, or selection utilizing a chaotic attractor function;
   to reassign the first pathological state to at least one candidate object in the plurality of candidate objects, or to at least one candidate object in a perturbed plurality of candidate objects, according to the one or more perturbed detection thresholds and/or perturbed detection probabilities; and to obtain updated pathology score data of the pathology sample based on the candidate objects having been reassigned the first pathological state according to the one or more perturbed detection thresholds and/or the perturbed detection probabilities, and to compare the initial pathology score data and the updated pathology score data to obtain a sensitivity of the pathology score data.

2. The apparatus according to claim 1,
wherein the one or more detection thresholds and/or detection probabilities characterise a variation in the automatic morphological feature detection when determining the presence of a candidate object in the digital pathology image data.

3. The apparatus according to claim 1,
wherein the one or more detection thresholds characterise a probability of automatic classification of the objects in the digital pathology image data into the plurality of candidate objects.

4. The apparatus according to claim 1,
wherein the detection threshold and/or the detection probability characterise an intensity level and/or a wavelength range of light emitted from a pathology sample and represented in the digital pathology image data.

5. The apparatus according to claim 4,
wherein the intensity level and/or the wavelength range emitted from the pathology sample and represented in the digital pathology image data indicate a relative level of the expression of a biomarker.

6. The apparatus according to claim 1,
wherein the processing unit is further configured to:
obtain a plurality of perturbed detection thresholds and/or perturbed detection probabilities and generate a sensitivity function of the pathology score of the digital pathology image data and optionally, to compute a relative detection threshold change necessary to provide a change in the pathology score.

7. The apparatus according to claim 1,
wherein the processing unit is configured:
to obtain the initial pathology score data and/or the updated pathology score data by counting the number of candidate objects in a field of interest of the digital pathology data having been assigned the first pathological state before and/or after perturbation, or by calculating a percentage score of the number of candidate objects in a field of interest of the digital pathology data having been assigned the first pathological state before and/or after perturbation.

8. The apparatus according to claim 1,
and wherein the processing unit is further configured:
to assign a second pathological state to at least one candidate object showing positive expression of a first biomarker of interest;
to assign a third pathological state to at least one candidate object showing negative expression of the first biomarker of interest, and
to obtain the initial pathology score data by performing a calculation using the candidate objects in the field of interest of the digital pathology data in the second and third pathological states;
to perturb the detection thresholds used to assign the second and third pathological states to the candidate objects and to reassign the second and third pathological states to the candidate objects after perturbation; and
to obtain updated pathology score data by performing a calculation using the candidate objects in the second and third pathological states after perturbation.

9. The apparatus according to claim 1, further comprising:
an output unit;
wherein the output unit is configured to output the sensitivity of the pathology score data to a user, optionally in combination with the initial and/or updated pathology score data and/or outputting the sensitivity of the pathology score relative to a clinical threshold.

10. The apparatus according to claim 9,
wherein the processing unit is further configured to spatially sub-sample the digital pathology image data into a plurality of sectors, and wherein the initial pathology score data and the updated pathology score is obtained for each sector, and wherein the processing unit is configured to generate a spatial sensitivity mask of the digital pathology image data using the initial pathology score data and the updated pathology score for the each sector; and
wherein the output unit is configured to display the spatial sensitivity mask to a user, optionally as a semi-transparent overlay in spatial alignment superimposed over the digital pathology image data.

11. The apparatus according to claim 1,
wherein the pathology sample is a histopathlogy sample or a cytopathology sample.

12. A digital pathology system, comprising:
a digital pathology image acquisition device; and
an apparatus according to claim 1,
wherein the digital pathology image acquisition device is configured to receive a pathology sample, to automatically analyze the pathology sample and to thus acquire digital pathology image data, and to communicate the digital pathology image data to the apparatus.

13. A method for digitally processing digital pathology image data to generate pathology score data, and a sensitivity analysis of the pathology score data, wherein the sensitivity analysis means an assessment of how the pathology score data are affected by perturbations to parameters used in the determination or generation of the pathology score data, the method comprising:
obtaining digital pathology image data comprising an image of a pathology sample;
classifying objects in the digital pathology image data into a plurality of candidate objects;
assigning a first pathological state to at least one candidate object in the plurality of candidate objects according to one or more detection thresholds and/or detection probabilities, wherein automatic morphological feature detection is utilized to identify the candidate objects;
obtaining initial pathology score data of the pathology sample based on the candidate objects in the plurality of candidate objects having been assigned the first pathological state;
perturbing the one or more detection thresholds and/or the detection probabilities according to a perturbation function to generate a perturbed detection threshold and/or a perturbed detection probability, wherein the perturbation function is configured to generate the perturbed detection threshold and/or the perturbed detection probability comprising selection utilizing a step function, random selection utilizing a probability distribution, selection utilizing a pre-provided range of values, selection utilizing an algebraic function, selection utilizing a random number generator, or selection utilizing a chaotic attractor function;

reassigning the first pathological state to at least one candidate object in the plurality of candidate objects, or to at least one candidate object in a perturbed plurality of candidate objects, according to the one or more perturbed detection thresholds and/or perturbed detection probabilities; and obtaining updated pathology score data of the pathology sample based on the candidate objects having been assigned the first pathological state according to the one or more perturbed detection thresholds and/or the perturbed detection probabilities, and comparing the initial pathology score data with the updated pathology score data to obtain a sensitivity of the pathology score data.

14. A non-transitory computer readable medium having stored thereon instructions that, when the program is executed by a computer, a processor, or a processing unit, cause the computer, the processor, or the processing unit to carry out the method of claim 13.

* * * * *